United States Patent [19]
Leveen et al.

[11] Patent Number: 5,830,172
[45] Date of Patent: Nov. 3, 1998

[54] ASCITES VALVE

[76] Inventors: Harry H. Leveen, 2173 St. James Dr., Charleston, S.C. 29412; Eric G. Leveen, 19 Palmetto Rd., Charleston, S.C. 29407

[21] Appl. No.: 566,972

[22] Filed: Dec. 4, 1995

Related U.S. Application Data

[63] Continuation-in-part of Ser. No. 683,821, Apr. 11, 1991, Pat. No. 5,520,632.

[51] Int. Cl.$^6$ .................................................. A61M 5/00
[52] U.S. Cl. .................................................. 604/9; 604/8
[58] Field of Search ............................. 604/8, 9, 10, 93, 604/128, 149

[56] References Cited

U.S. PATENT DOCUMENTS

| | | | |
|---|---|---|---|
| 3,683,929 | 8/1972 | Holter | 604/9 |
| 3,768,508 | 10/1973 | Schulte | 604/9 |
| 3,886,948 | 6/1975 | Hakim | 604/9 |
| 3,910,283 | 10/1975 | LeVeen | 604/9 |
| 4,261,341 | 4/1981 | Hamim et al. | 604/9 |
| 4,332,255 | 6/1982 | Hakim et al. | 604/9 |
| 4,464,168 | 8/1984 | Redmond et al. | 604/9 |
| 4,475,899 | 10/1984 | Muller | 604/9 |
| 4,553,956 | 11/1985 | Muller | 604/9 |
| 4,636,194 | 1/1987 | Schulte et al. | 604/8 |
| 4,650,463 | 3/1987 | LeVeen et al. | 604/128 X |
| 4,662,404 | 5/1987 | LeVeen et al. | 138/12 |
| 4,795,437 | 1/1989 | Schulte et al. | 604/10 |
| 4,867,740 | 9/1989 | East | 604/9 |
| 4,904,236 | 2/1990 | Redmond et al. | 604/9 |
| 4,904,241 | 2/1990 | Bark | 604/93 |
| 5,026,344 | 6/1991 | Dijkstra et al. | 604/93 |
| 5,304,114 | 4/1994 | Cosman et al. | 604/8 |
| 5,385,541 | 1/1995 | Kirsch et al. | 604/8 |
| 5,411,473 | 5/1995 | Ahmed | 604/8 |
| 5,486,165 | 1/1996 | Stegmann | 604/8 X |
| 5,520,632 | 5/1996 | LeVeen et al. | 604/8 X |
| 5,584,314 | 12/1996 | Bron | 604/8 X |

FOREIGN PATENT DOCUMENTS 8301387  4/1984  WIPO.

OTHER PUBLICATIONS

Harry H. LeVeen et al, Coagulopathy Post Peritoneovenous Shunt, Mar. 1987, p. 305, Annals of Surgery vol. 205, No. 3.

Harry H. LeVeen, The Peritoneovenous Shunt, Apr.–Jun. 1993, p. 50 ASAIO, vol. 36, No. 2.

*Primary Examiner*—Sam Rimell
*Attorney, Agent, or Firm*—Gipple & Hale; John S. Hale

[57] ABSTRACT

A device for the transfer of body fluids which accumulate in the peritoneum cavity into the vascular system comprising a peritoneal tube connected to the inlet chamber of a hollow plastic implanted valve assembly, causing a valve to open and passing the fluid under pressure into a second chamber from where the fluid is conducted through a venous tubing which is connected to the jugular vein of the patient. The valve assembly comprises a plastic housing with an inlet and outlet, the peritoneal tube being secured to the inlet leading to an inlet reservoir located within the valve housing and the venous tube being secured to the outlet leading from the outlet reservoir located within the valve housing. The valve housing defining a valve seat and having a flexible diaphragm valve which rests against the valve seat and moves away from said valve seat in response to pressure exerted thereon to permit flow of the body fluid from the peritoneum through the valve housing and into the venous tubing which is threaded into a major intrathoracic vein via the internal jugular vein or other alternate access veins.

16 Claims, 7 Drawing Sheets

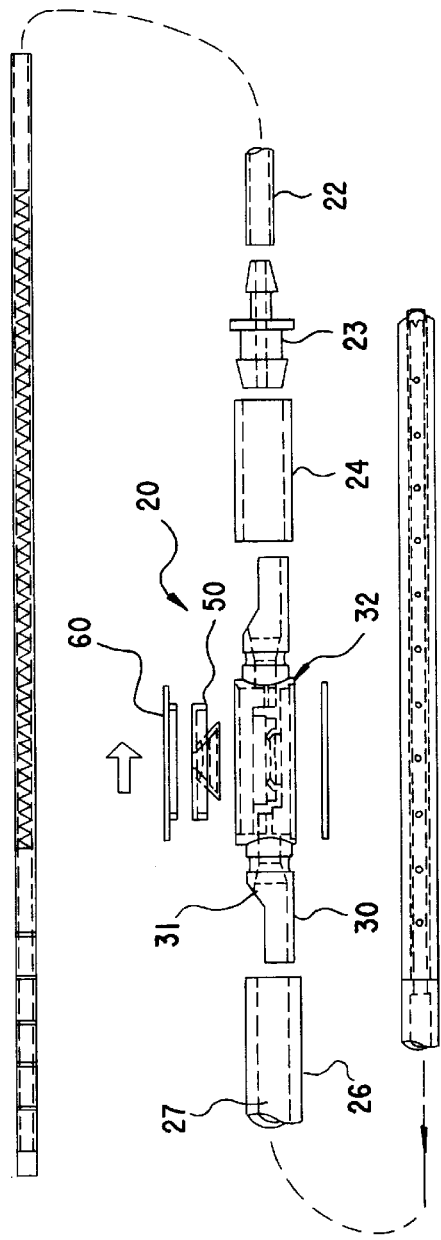
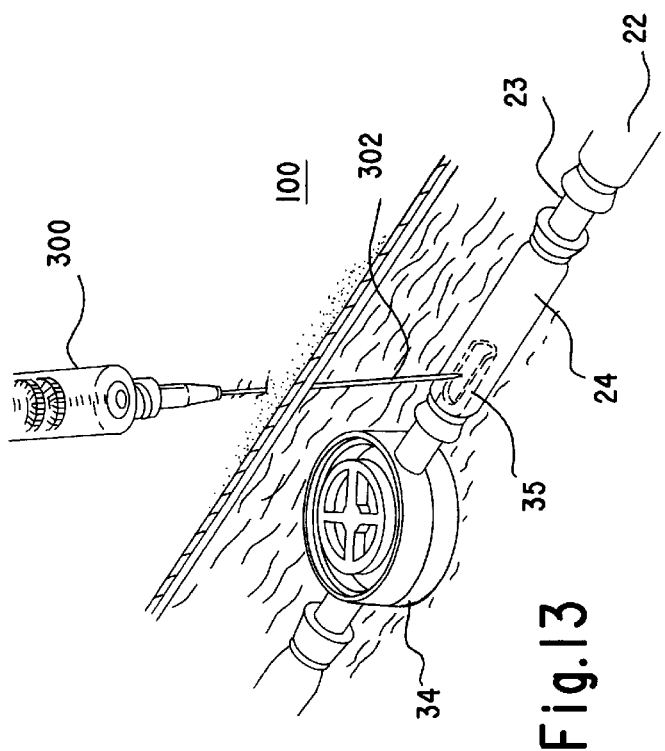
Fig.1
Fig.13

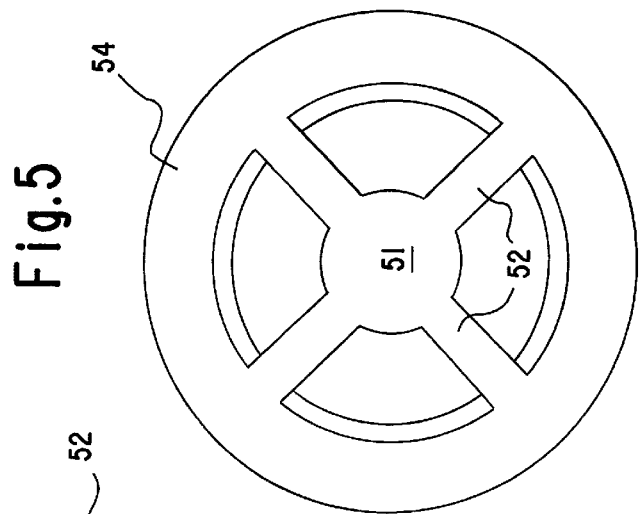
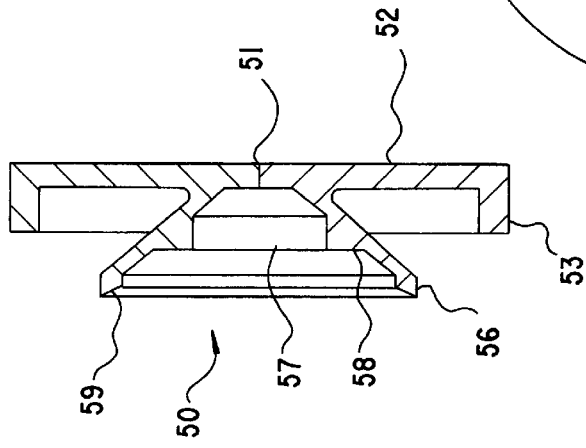
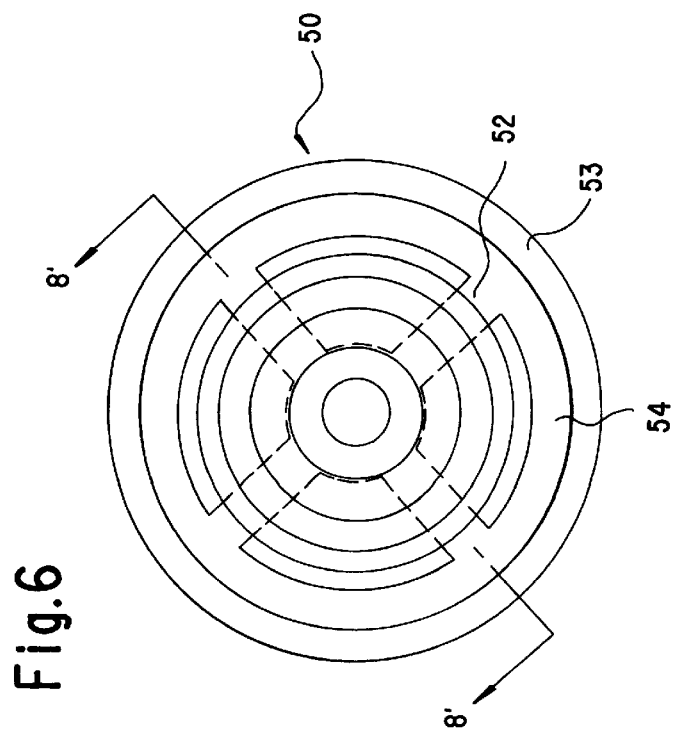
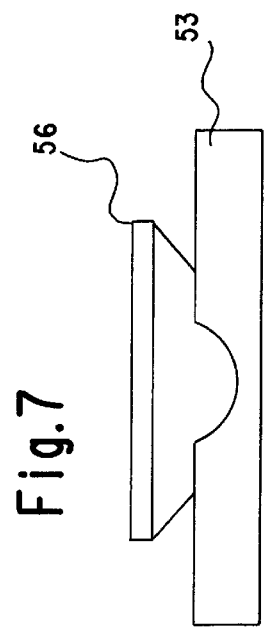

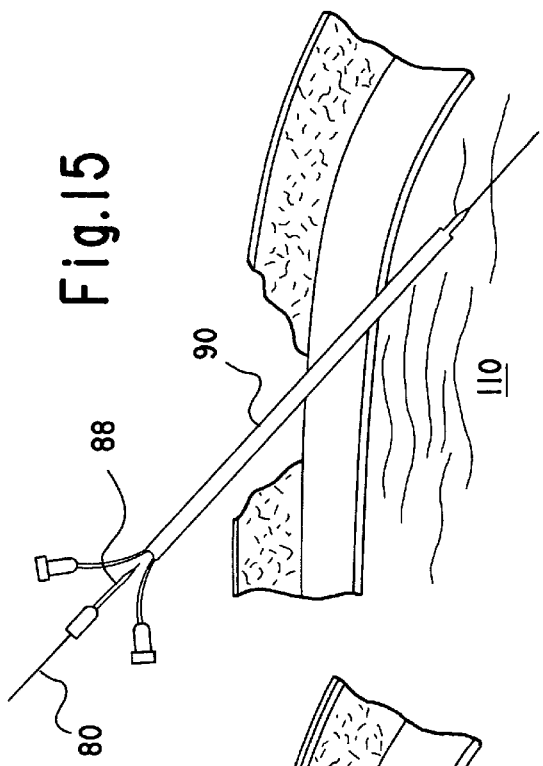
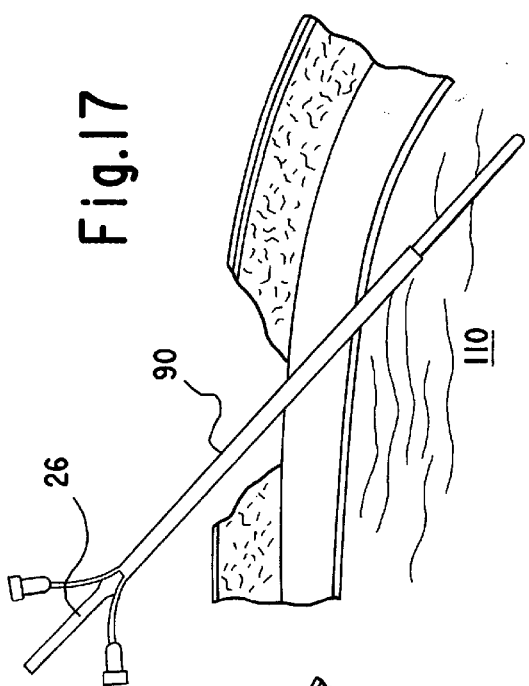
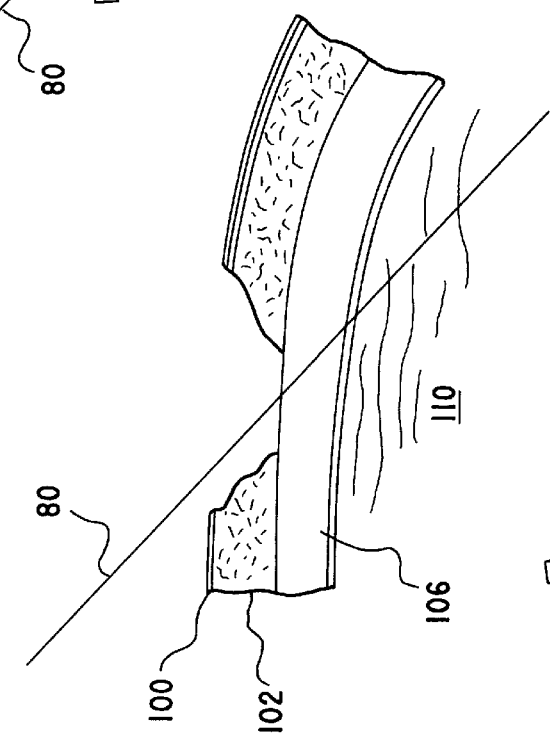
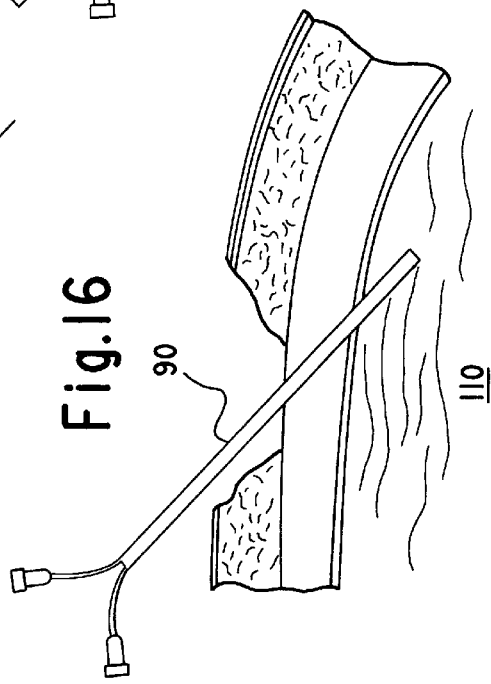

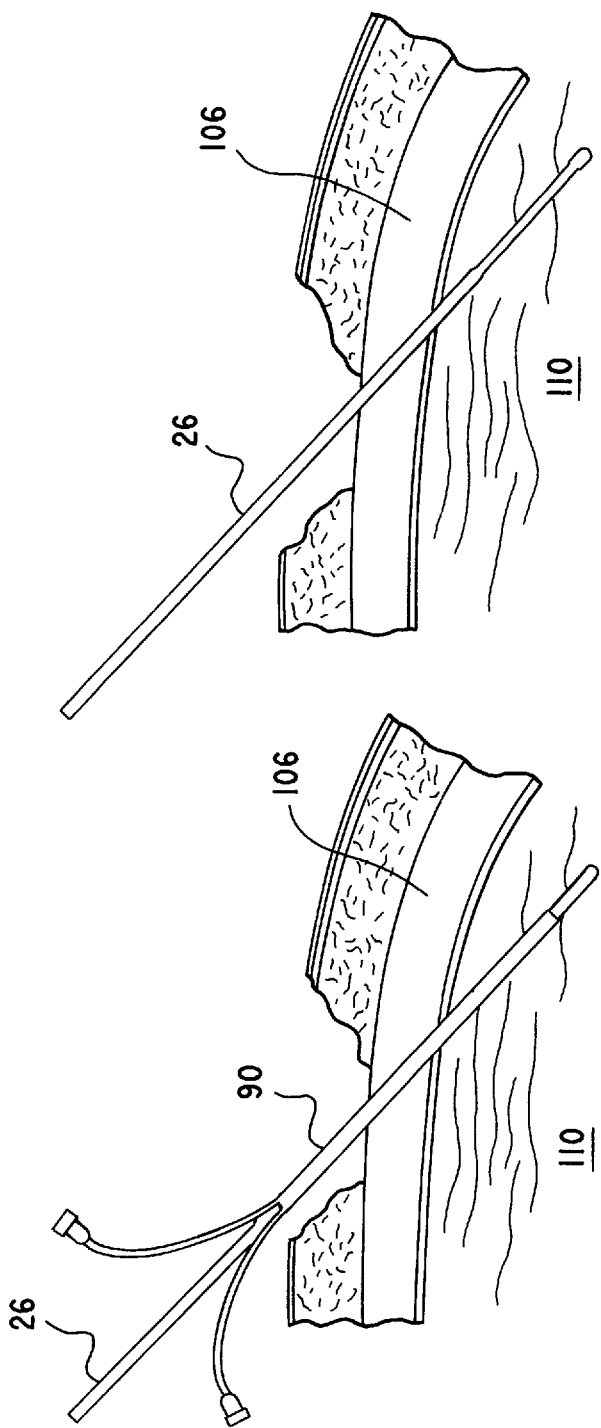

ASCITES VALVE

RELATED CASES

The present application is a continuation-in-part application of Ser. No. 07/683,821 filed Apr. 11, 1991 now U.S. patent application Ser. No. 5,520,632 issued May 28, 1996.

BACKGROUND OF THE INVENTION

Ascites is a common complication of cirrhosis and carcinoma. Its presence significantly worsens the prognosis. A high percentage of patients having cirrhosis who do not respond to a salt restricted diet are dead within a year. Mortality in such patients is due to renal failure brought about by diminished renal perfusion secondary to a diminished blood volume (Clairmont, R. J., Gastroenterol., 1967, 53:220–228). The peritoneovenous (P-V) shunt has been a significant advance in the therapy of this condition. Ascitic fluid has its ultimate origin from blood and should be returned to the circulating blood from where it arose. The peritoneovenous shunt drains ascitic fluid from the peritoneal cavity via flexible tubing through a sensitive, one-way, pressure activated valve into a tube whose tip is located in a major thoracic vein. The shunt system thus continuously infuses ascitic fluid into the blood. The descent of the diaphragm during respiration lowers the pressure in the thorax to below atmospheric pressure enabling air to enter the lungs. The force required to pump the fluid is supplied by a differential pressure between the peritoneal fluid and a large intrathoracic vein. This differential pressure is brought about by a negative intrathoracic pressure which occurs during respiration with descent of the diaphragm and a simultaneous increase in intraperitoneal pressure as the descent of the diaphragm decreases the volume of the peritoneal cavity. Once the fluid gains access to the circulating blood, the body excretes any excess fluid as urine. Although excessive amounts of water and salt are excreted by the kidney, the plasma proteins present in the ascitic fluid are retained.

Flow sensitive valves require a small amount of backflow to close the valve orifice. A small amount of backflow into the venous tubing will obstruct it with clots. A normally closed sensitive pressure activated valve is mandatory to prevent regurgitation of blood into the tubing (LeVeen, H. H., Ann.Surg., 1974, 180:580) and such a normally closed pressure sensitive valve prevents backflow of blood into the venous tubing which would obstruct the lumen with clots. An obstruction to the free flow of ascitic fluid into the venous system results in failure of the shunt. Although the valve must be normally closed, the valve must open at very low pressures (1 to 4 cm of water) since the differential pressures which supply the necessary pumping force are extremely low. The diaphragm of the valve is manufactured of a low durometer biocompatible elastomer such as silicone rubber and is provided with the struts which suspend the diaphragm over the valve's seat. The struts being elastomeric, elongate with pressure and allow the diaphragm to rise and open the valve at low pressures.

Studies about the effectiveness of the P-V shunt in cirrhotic ascites, as compared to medical therapy, have given little or no consideration to refinements in surgical care. Even without these advances, the survival of patients with P-V shunts is superior or equal to medical therapy and the quality of life of the patient is much improved. The short and long term surgical mortality was stated to equal that of the medical mortality in a recent large randomized study. However, close inspection of the clinical material in this study demonstrates that the P-V shunt is really statistically superior to medical therapy. The cause and successful treatment of post shunt coagulopathy (PSC) was well known at the time of this comparative trial. Epsilon aminocaproic acid is the antidote which prevents and cures post shunt coagulopathy; yet, there were five avoidable surgical deaths from PSC which went untreated. The shunted group would have had a statistically significant longer early and late survival than the medically treated group. Of the 153 patients treated medically, 43 (28%) died. If one excludes the 5 deaths from post shunt coagulopathy, of 146 cases treated surgically, only 26 would have died (18%). Also, 10% of the patients who failed medical therapy were shunted, thus exposing that group to the dual mortality of both medical and surgical treatment.

Most criticisms of the P-V shunt have involved the incidence of failed shunts and the frequency with which shunts must be replaced. If any reduction of shunt failure is to be achieved, the cause for failure must be determined. This has been done in 65 failed shunts and 16 additional cases have been subsequently added including cases studied by others. The failures were subsequently divided into early and late categories. Early failures occurred in the immediate postoperative period. More than half of the early failures were due to errors such as malplacement of the tip of the venous tube. In placing central venous catheters, malposition of the tip occurred in 20–30% of insertions. This approximates the number of shunt malplacements. The tip of the venous tubing must be in the vena cava at the atriocaval junction but not in the atrium. Surgeons placing central venous lines in cancer patients observed a significant increase in thrombosis if the catheter tip was above the T-3 level. Others have confirmed that if central venous catheters do not extend far enough into the superior vena cava, the risk of thrombosis is greater. Malplacements of the tip of the venous tubing must be detected during surgery by the mandatory use of x-rays.

Some surgeons perceive a pump to flush the venous line as a technical benefit; but, in reality, it is a hazard and fails to reestablish shunt patency or provide any positive diagnostic information on the cause of failure. Only a physician should introduce fluid into the venous line and then no more than 5 cc. When performing a shuntogram only 5 cc of contrast agent is injected to avoid pulmonary embolization. A fatal pulmonary embolus occurred in a known patient when a radiologist injected fluid into the venous line and dislodged a caval thrombus.

In the prior shunt disclosed in the parent application, the valve was designed to be placed between the layers of the abdominal wall. This made watertight closure a problem and leakage of peritoneal fluid occasionally occurred through the sutured wound edges. Fluid leakage is almost always associated with local infection, a serious complication. Although surgeons were cautioned that the wounds must be watertight, there was nonetheless a significant incidence of local infection reported in the literature. The configuration of the body of the valve has now been changed so it lies in the subcutaneous tissue and the peritoneal cavity is entered with a dilator and a peel-away introducer through which the peritoneal collecting tube is inserted. This prevents leakage, simplifies the surgery and shortens the operative time.

Late shunt failures are frequently caused by occult bacterial peritonitis. Surgeons are usually only aware that a shunt has failed and the ascites has returned. During replacement of the shunt, the presence of fibrin flecks in the peritoneal fluid is noticed. The peritoneal fluid normally contains all plasma. However, plasminogen and fibrinogen are exceptions since they are absent or present only in trace amounts in the peritoneal fluid. The peritoneum secretes copious quantities of tissue plasminogen activator into the peritoneal fluid which converts plasminogen to plasmin. The plasmin then converts fibrinogen to split products. This active fibrinolysis in the peritoneal fluid makes shunt placement possible by preventing clot formation in the vena cava. Fibrinolysis in the peritoneal cavity explains why blood in the peritoneal cavity does not clot and why autotransfusion is possible. This fibrinolysis can be prevented by neutralizing the tissue plasminogen activator with epsilon aminocaproic acid (EACA). Post shunt coagulopathy is present, peritoneal fibrinolysis has been widened to include the vascular system and EACA must be administered systemically. Discarding most of the ascetic fluid at surgery also has eliminated serious PSC.

In the presence of peritoneal infection, the secretion of tissue plasminogen activator ceases and intraperitoneal clotting occurs. Hence, "fibrin flecks" are present in the peritoneal fluid in peritonitis. Although these particles have been called "fibrin flecks" by surgeons, they are, in reality, fibrinoprulent exudates caused by occult peritonitis. The condition should be diagnosed by paracentesis prior to shunt replacement. It is believed that thorough irrigation of the abdomen with a wide spectrum antibiotic (including gram negative organisms) makes it safe to implant a new shunt using the same venous tubing. The pathogenesis of occult bacterial peritonitis is usually a mild enterocolitis causing a portal bacteremia of gram negative organisms. Because a portion of the portal venous blood bypasses the liver and because a reduced RE system in cirrhotic livers fails to remove all of the bacteria from portal blood a systemic bacteremia ensues. These circulating gram negative bacteria gain access to the peritoneal fluid via the circulation. Bacteria flourish in the relatively acellular peritoneal fluid. An occult low grade peritonitis ensues. The initial incidence of occult peritonitis in new admissions for ascites has been found to be between 19% and 36% of those patients with hepatic encepalopathy. When occult peritonitis occurs in shunted patients, the shunt usually fails because "fibrin flecks" occlude the valve. These "fibrin flecks" should be cultured and smears made for microscopy if their true nature is to be identified. The use of a pump by a surgeon or patient in such circumstances would disseminate the infection and lead to septic thrombophlebitis in the vena cava. Therefore, a pump should not be incorporated into a P-V shunt system.

Occult peritonitis is usually mild and signs of sepsis are rarely present. In a series of more than 450 patients, five patients were encountered at initial surgery with frank peritonitis and milk like opacity of the peritoneal fluid. Three of these patients were treated with antibiotics awaiting the subsidence of the peritonitis. These patients died in hepatorenal syndrome with tense ascites. In the subsequent two patients, the peritoneum was irrigated with antibiotics and a peritoneovenous shunt implanted. These patients had an unremarkable postoperative course.

Recent thrombi can be successfully treated with urokinase. However, a thrombus older than 2½ weeks is rarely susceptible to lysis. Early thrombosis is usually no a septic thrombosis and if the thrombus is dissolved the patient should be kept on heparin for 2 or 3 weeks after reestablishing patency.

DESCRIPTION OF THE PRIOR ART

PCT Application Number 8301387 discloses a cylindrical peritoneovenous shunt for draining ascites fluid which utilizes a conventional pressure sensitive normally closed valve in the shunt and is provided with a manually manipulatable flushing chamber. The shunt has a normally open flow sensitive valve on the inlet side of the shunt and incorporates a pump which can be compressed to clear the valve and shunt system. It was not known at the time of development of the '387 shunt that occult peritonitis occurred in 10% of patients with cirrhotic ascites.

Numerous studies are recorded in a published paper on post shunt coagulopathy Annals of Surgery Vol. 205, No 3, March 1987 p. 305 entitled Coagulopathy Post Peritoneovenous Shunt and a referenced shunt to solve the noted problems is discussed in ASAIO, April–June 1993 Vol. 36, No. 2 p.50 entitled The Peritoneovenous Shunt.

In U.S. Pat. No. 4,553,956 a shunt is disclosed which is implantable and is constructed with a housing which contains an inlet conduit for receiving ascites fluid from the peritoneal cavity of the patient and an outlet conduit in fluid communication with the inlet conduit for delivering ascites fluid into the vascular system of the patient. A valve seat is positioned intermediate the inlet conduit and the outlet conduit and a normally closed valve diaphragm is movably positioned in the housing resting against the valve seat. A normally collapsed expansible balloon is positioned in the inlet conduit and when the balloon is expanded it occludes the inlet conduit thus preventing ascites fluid from reaching the valve diaphragm.

In U.S. Pat. No. 3,910,283, the flexible diaphragm valve of the valve is shown occupying the transverse diameter of a cylindrical rigid opaque plastic housing. The resistance (R) to flow of Newtonian fluids through a tubular structure depends on the length (L) and radius (r) of the tube and the viscosity of the fluid (z) according to the equation of Poiseuille:

$$R = \frac{8Lz}{nr^4} \text{ (Poiseuille's Law)}$$

In the '283 Patent, the inflow and outflow ports of the valve are at the opposite ends of a circular housing. Regurgitation of blood was prevented since the valve was normally closed with sufficient sensitivity to open at differential pressures of 1 to 4 centimeters of water.

The physical configuration of the '283 valve is unsatisfactory since the housing is large in its transverse diameter because the transverse diameter of the elastomeric diaphragm is very large. Since the valve body or housing was fabricated of relatively opaque rigid plastic (polypropylene), the opening and closing of the valve during respiration could not be detected at surgery. However, it is necessary that the surgeon confirm that the valve is functioning before closing the incisions. The cylindrical housing of the valve of the '283 Patent is cumbersome since the valve must occupy a considerable depth in the subcutaneous tissue. Ideally, the largest dimension of the housing enclosing the diaphragm should lie in the same plane as the subcutaneous fatty tissue which is parallel to the skin.

SUMMARY OF THE INVENTION

In the present invention, the configuration of the valve housing is that of a thin disc with the largest dimension of the housing lying parallel to the skin and subcutaneous fatty tissue. This avoids the lump previously caused by the large mound of tissue necessary to cover the valve. A valve housing made of a biocompatible transparent plastic is configured so that the inflow and outflow open faced conduits provide fluid communication with chambers of the thin disc shaped housing. Transparency not only allows the surgeon to observe valve function but permits the detection of fibrin deposits, blood or debris in the ascitic fluid. The large transverse diameter of the housing lies in the plane of the skin and subcutaneous tissue without causing a protusion. An arrow on the upper surface of the valve shows the direction of flow. This warns against inadvertently connecting the valve in the reverse direction of flow. The elastomeric frustrum conical diaphragm of the valve is limited in movement by a transparent top lid which is mounted to the housing. The inlet and outlet conduit portals have their top surfaces removed to allow needle access with the base portions providing a safety stop for the needle.

In the present P-V shunt heparin was bonded chemically to the outer surface of the tip of the venous tubing to ameliorate early clotting. Heparin bonding of intravenous catheters has significantly reduced the incidence of thromobotic complications. There was found to be no significant gain in flow dynamics in non-viscid fluids by increasing the diameter of the venous tubing beyond that of 12 French. Any reduction in impedance with diameters larger than 12 French fail to improve flow rates of non-viscid fluids through catheters. Therefore, the size of the venous tubing has been reduced to 12 French. It was also found that a vertical radiopaque stripe on the venous tubing to aid in radiological identification causes the tube to be stiffer on one side predisposing it to curve in the direction of the stripe promoting malposition of the tip. Therefore, the striped tubing has been replaced with a uniform lightly opacified tubing making x-ray visualization obvious. The tubing is further opacified during a shuntogram. The smaller size of the venous tubing (12F) makes it possible to introduce it through either the subclavian or internal jugular vein using a peel away introducer. Since the tip of the venous tubing is heparinized, the tubing must be shortened by cutting excess tubing from the valve end.

The casing of the valve in the present invention is rigid since distortion of the valve case can lead to momentary deformation of the valve with resultant back flow. An ascitic fluid/blood interface must always be maintained at the tip of the venous tubing to prevent blood from seeping into the venous tubing and clotting thus obstructing the venous tubing. Leakage of a valve always provokes clotting within the tubing. Leakage at high pressures is unlikely since a high differential pressure ensures a tight seal. Since leakage at low pressures is a problem, every valve used for a peritoneovenous shunt must be tested with air and the opening and closing pressures of each valve verified before sterilization. Random samples are taken for testing and culture post sterilization. Tests must be done to assure the valve will maintain a pressure of 3 cm of water without subsequent pressure loss.

Because a shuntogram is so essential to the diagnosis and treatment of shunt failure, injection ports have been incorporated into the present inventive shunt system. The stems of both the outlet and inlet portals have been unroofed so that a noncoring 22 gauge needle can be inserted into the outlet or inlet tubing without the danger of leakage at the puncture site or perforation of the posterior wall. This facilitates performing a shuntogram and simplifies the injection of urokinase to dissolve fresh thrombi.

The modular design of the present invention permits an easy replacement of any failed part. The individual replacement of the failed part of the shunt is therefore possible without removal of the entire shunt system. Fresh clots in the venous tubing or vena cava can be dissolved by injecting fibrinolysins. Reopening of a clotted venous tubing often prevents a second neck incision which is painful to the patient and distressing to the surgeon.

In the accompanying drawings, there is shown an illustrative embodiment of the invention from which these and other of objective, novel features and advantages will be readily apparent.

BRIEF DESCRIPTION OF THE DRAWINGS

FIG. 1 is an exploded view of the inventive peritoneovenous shunt assembly with the end of the peritoneal tubing and the end of the venous tubing being enlarged;

FIG. 5 is a top plan view of the valve of the inventive shunt assembly of FIG. 1;

FIG. 6 is a bottom plan view of the valve of the inventive shunt assembly of FIG. 5;

FIG. 7 is a side elevational view of the valve shown in FIG. 6;

FIG. 8 is a cross sectional view of the valve of FIG. 6 taken along lines 8'—8'of FIG. 6;

FIG. 13 is an enlarged perspective view of the disc shaped valve housing implanted in the patient with unroofed inlet and outlet ports shown in phantom with peritoneal and venous tubing fastened to the inlet and outlet ports and a syringe inserting fluid into the valve outlet chamber;

FIG. 14 shows a schematic insertion of a guide wire into the peritoneal cavity;

FIG. 15 shows a schematic sequential insertion of the dilator and strip tube over the guide wire into the peritoneal cavity;

FIG. 16 shows a schematic sequential removal of the guide wire and dilator from the strip tube;

FIG. 17 shows a schematic sequential insertion of the peritoneal tubing through the strip tube into the peritoneal cavity;

FIG. 18 shows a schematic sequential of how the introducer is peeled away from the peritoneal collecting tube;

FIG. 19 shows a schematic sequential after removal of the introducer leaving the peritoneal tubing in the peritoneal cavity;

DETAILED DESCRIPTION OF THE DRAWINGS

Figure 2:
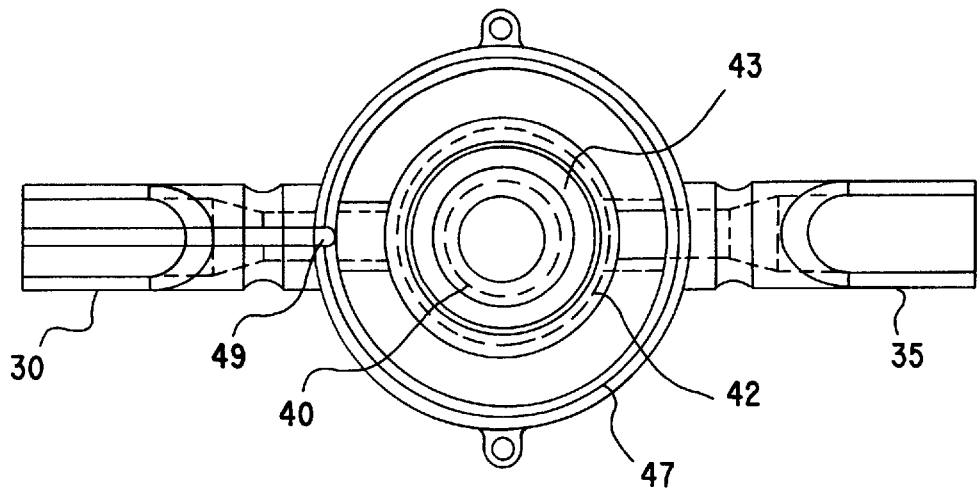
FIG. 2 is a top plan view of the valve housing of the inventive shunt assembly of FIG. 1 with the top cap removed.

The peritoneal shunt of the present invention has been designed to prevent the aforementioned complications which are noted as occurring in the prior art. The preferred embodiment and best mode of the invention is shown in FIGS. 1–13.

FIG. 1 shows an exploded view of the ascites shunt assembly 20. The various component parts are welded together by heat sealing or adhesives rather than by threaded members which are prone to leak. The flexible venous tubing 22 is shown broken away with nipple adapter 23 and outlet tubing 24. The peritoneal tubing 26 is also shown broken away.

That portion of the peritoneal tubing which perforates the abdominal wall preferably has a circular cross section with a diameter which does not exceed 12 French in size. The peritoneal tubing 26 can be provided with throughgoing longitudinal slits and/or throughgoing perforations into its center lumen 27. The end portion as shown in FIG. 1 of the peritoneal tubing 26 which perforates the abdominal wall has an outside shape which is rounded and without protuberances or slits. That portion of the tubing which is inside the peritoneal cavity has long longitudinal slits on the outer circumference of the tube. These slits open into an inner lumen 27 via the perforations and allow any incarcerated omental lobules to slide along the slit during removal of the tube, thus preventing their avulsion. That part of the collecting tube which exits the abdominal wall is circular and contains no slits to ensure a leak free seal between the tube and the abdominal wall. The tubing permits easy insertion and removal since it has a smooth outer circular configuration. The peritoneal tubing is easily inserted into the peritoneal cavity by means of an introducer utilizing the Seldinger technique.

Figure 3:
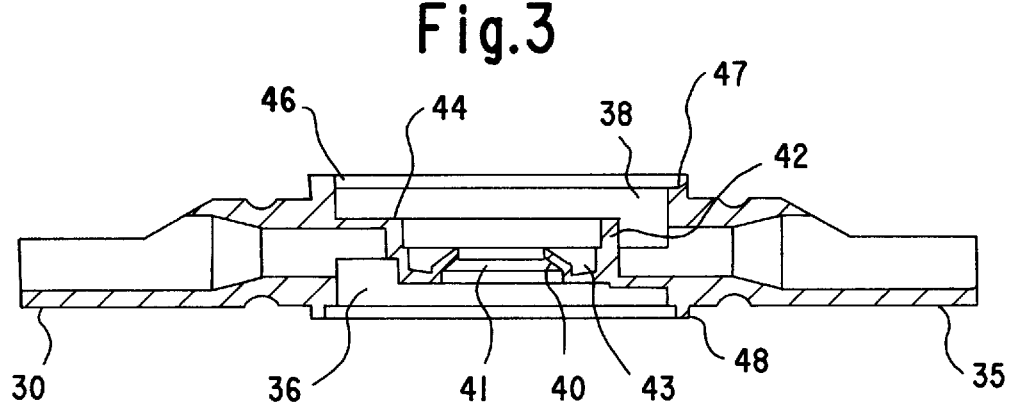
FIG. 3 is a cross sectional view of the valve housing of FIG. 2 taken along lines 3'—3'of FIG. 2.
Figure 4:
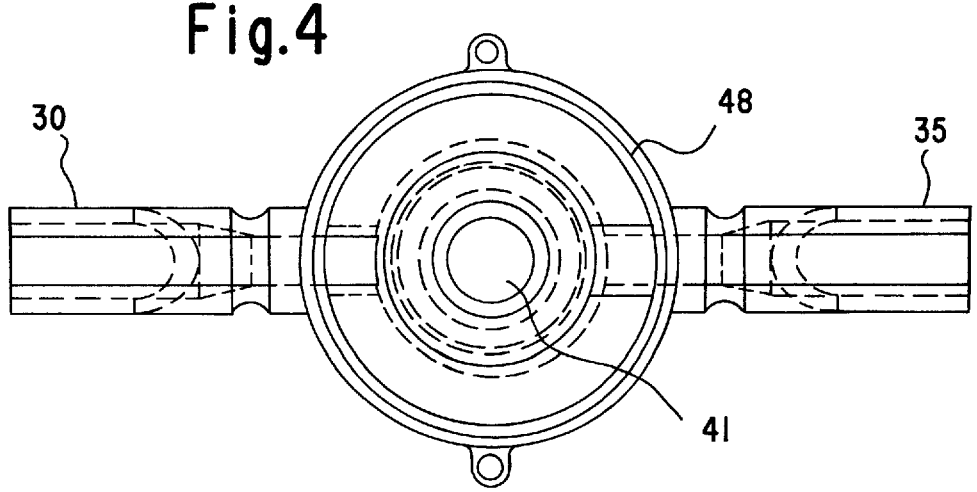
FIG. 4 is a bottom plan view of the valve housing of the inventive shunt assembly of FIG. 2 with the bottom cap removed.
Figure 9:
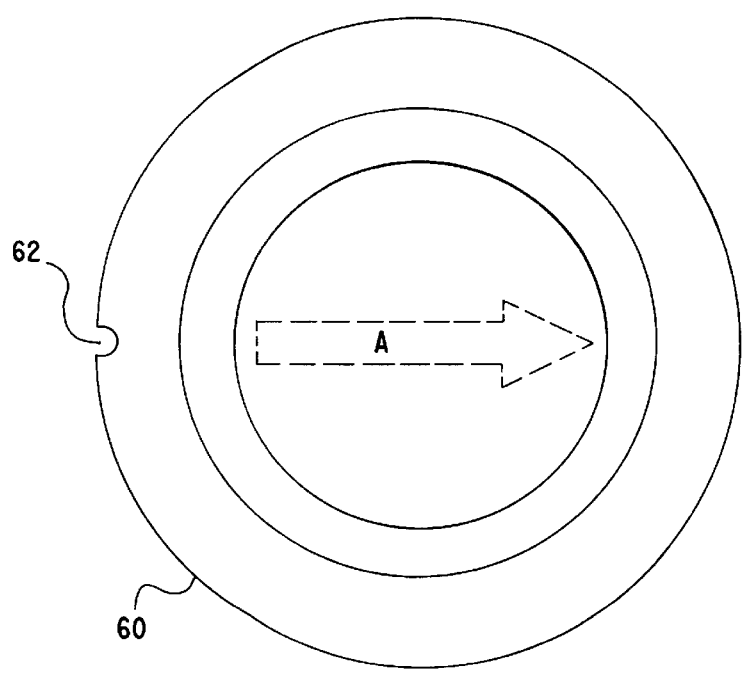
FIG. 9 is a bottom plan view of the valve housing top cap of the inventive shunt assembly of FIG. 1.
Figure 10:
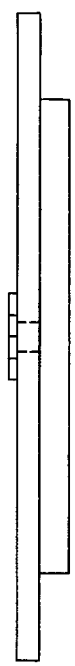
FIG. 10 is a side elevational view of the valve top cap shown in FIG. 9.
Figure 11:
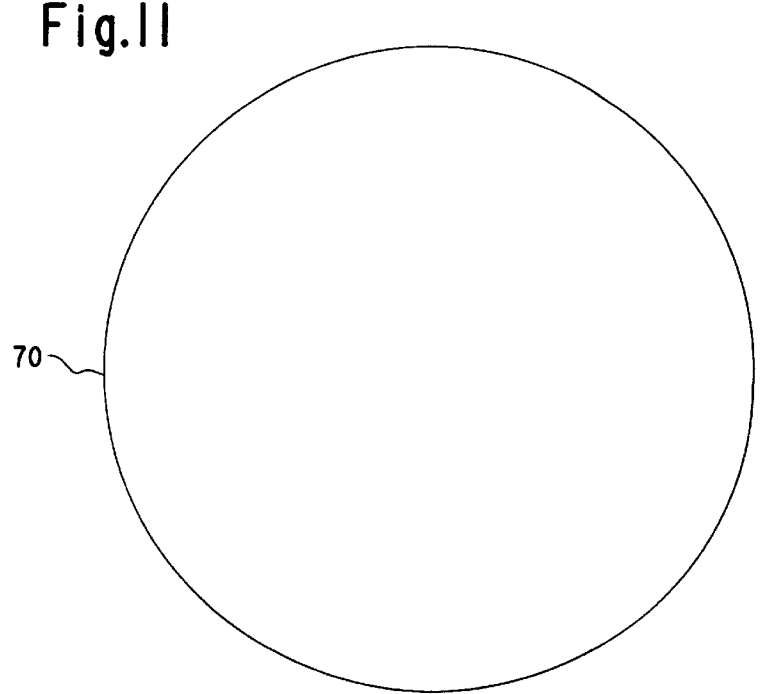
FIG. 11 is a bottom plan view of the valve housing bottom cap of the inventive shunt assembly of FIG. 1.
Figure 12:
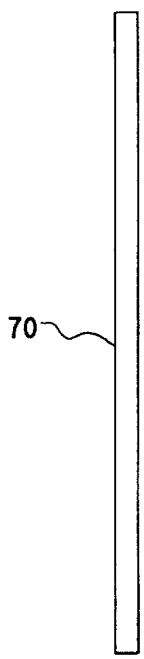
FIG. 12 is a side elevational view of the valve housing bottom cap shown in FIG. 11.

The peritoneal collection tubing 26 is attached to an open faced inlet conduit connector 30 which forms the inlet port 31 for the valve housing 32. The rigid cylindrical body 34 of the valve housing 32 is formed with two separated compartment chambers, namely inlet chamber 36 and outlet chamber 38. The housing 32 is fabricated of transparent plastic such as polysulfone so that the surgeon may see the valve open and shut during respiration. The body of the cylindrical valve is made of a transparent biocompatible plastic which has good optical clarity and engineering plastic properties and is integrally molded with an intermediate truncated conical valve seat 40 defining a central fluid communication port 41 which is circular with diameter of about 0.230 inches. The valve seat projects into the outlet chamber 38 and is surrounded by a stepped cylindrical side wall 42. The inner surface of the side wall 42 is spaced approximately 0.125 inches from the base of the valve seat 40 to form an annular channel 43 which is angled downward as shown in FIG. 3 to receive and support valve 50. The side wall and valve seat divide the valve housing into an inlet chamber or reservoir and an outlet chamber or reservoir. The top of side wall 42 is formed with a planar surface 44 to form a seat for rim flange 53. A top cover 60 with an arrow marking indicia A rests in cover seat 46 formed on the housing 32 with the circumference of the cover abutting the inner wall 47 of valve housing 32. The top cover 60 defines a small recess 62 which fits on nipple 49 so that the cover is always properly aligned to show fluid flow direction. A bottom cover 70 is secured to the bottom of the cylindrical valve housing in cover seat 48 in the same manner as previously described for top cover 60, namely by adhesives or sonic welding. However, if desired, the covers could be snap fit into grooves cut in the inner wall surface 47. The top surface of the housing defines a stepped circular opening 46 which receives top cover or cap 60 while the bottom surface of the housing defines a similar stepped circular opening 48 which receives a bottom cover or cap 70.

The valve member 50 which is preferably integrally formed as best seen in FIGS. 5–8 is used in the valve housing and rests on valve seat 40. The diaphragm valve 50 offers the lowest resistance to flow as compared to other configurations, e.g., a spring loaded ball valve or a duck bill valve. When open, a diaphragm valve offers little resistance to flow because the diaphragm can cover an opening of large cross sectional area thus amplifying the opening force and reducing resistance to flow. The valve member 50 has a plurality of at least four elastomeric struts 52 extending from a central circular support area 51. The struts 52 distal ends are connected to and reinforced by an annular rim member 54 which has a downwardly projecting flange 53. The central support area 51 is provided on its inner surface with a frustrum conical diaphragm member 56 which sits on seat 40 covering port 41. The diaphragm member 56 defines a hollow chamber 57 with an annular step seat 58 and an angled end 59. As previously noted, the diaphragm member 56 sits on seat 40 and is held in place by the angled end 59 which downwardly projects into space 43 and the inner surface of cylinder side wall 42. Thus the valve is kept in the normally shut position. The differential pressure of 1–4 cm of water raises the valve diaphragm stretching the elastomeric struts and lifts the valve diaphragm 56 above the valve seat orifice 41. The diaphragm of the valve is manufactured of a low durometer silicone rubber together with the struts which suspend the diaphragm over the valves inlet orifice. The struts being elastomeric elongate with pressure and allow the diaphragm to raise and open the valve at low pressures.

It will be apparent to anyone skilled in the art that the thickness of the elastomeric struts 52 are important in determining the opening pressure of the valve and the resistance to flow through the valve at low differential pressures. Also important in the opening pressure is the degree of tensile strain on the struts in the closed position. If there is practically no tension on the struts the opening pressure will be low. While a low opening pressure is important in ascites as previously described, in the ventriculoperitoneal shunt for hydrocephalus, the opening pressure must be higher to avoid sagging of brain tissue. In hydrocephalus the sensitivity must not be as low as required for ascites since the volume of the fluid to be cleared is far less than in ascites and large fluctuations in pressure and volume must be avoided. Thicker struts dampen fluctuations and tend to maintain a mean pressure which is very desirable in the therapy of hydrocephalus. The design of the valve itself therefore lends itself to usage for conditions other than ascites such as hydrothorax and hydrocephalus.

The venous tubing 22 is circular and thin walled. The venous tubing 22 is attached to a nipple shaped connector 23 which is mounted to the outlet port conduit 35 of valve housing 32.

FIG. 13 shows a syringe 300 and needle 302 inserted through the skin 100, subcutaneous fatty layer 102 into the outlet conduit 35. A syringe attached to the needle makes it possible to inject medicaments or radio opaque compounds into the outlet side of the valve and the venous tubing.

The insertion of the peritoneal and venous tubing into the patient 200 is shown in FIGS. 14–19.

FIG. 14 shows a guide wire 80 inserted through the abdominal wall 106 into the peritoneal cavity 110.

FIG. 15 shows a dilator 88 and an introducer 90. The dilator 88 is inserted over the guide wire 80 to a diameter which will allow the passage of the peritoneal tubing 22.

In FIG. 16 the introducer 90 is shown after removal of the dilator and guide wire.

In FIG. 17 the peritoneal tubing 26 has been inserted through the introducer 90.

In FIG. 18 the introducer 90 is split by pulling it apart and removing it.

In FIG. 19 the peritoneal tube 26 is seen in the peritoneal cavity 110.

In FIGS. 14–19 a subcutaneous incision is made at a suitable site on the upper abdomen to expose the abdominal musculature. A needle is diagonally inserted into the peritoneal cavity 110 through the abdominal musculature 106. A flexible guide wire 80 is introduced through the bore of the needle which is then removed leaving the guide wire in place. In FIG. 14 a dilator 88 and introducer sheath 90 are placed over the guide wire 80 and the small needle hole is dilated to the size which will accommodate the splitable introducer 90 shown in FIG. 15. The rigid dilator 88 is then removed leaving the circular introducer 90. Before removing the introducer, some surgeons prefer to aspirate some peritoneal fluid. After an appropriate quantity has been removed, the peritoneal collection tube 26 is inserted as shown in FIG. 17 and the introducer is removed by splitting the two sides (FIG. 18).

The lower section of the peritoneal collecting tube 26 is positioned in the peritoneal cavity 110. The upper part of the tube 26 contains no slits and fits so tightly in the tissues 100–108 that there is little or no leakage of ascitic fluid around its circumference. Further aspiration of fluid can also be done at this time before connecting the peritoneal tubing to the valve. Leakage of ascitic fluid constituted a problem when the shunt in U.S. Pat. No. 3,910,283 was inserted, because it required incision to be made into the peritoneal cavity 110. A subsequent difficulty occurred in completing a water tight closure of the peritoneum 108 around the valve which is predisposed to leakage.

The present invention utilizes an introducer which requires only a needle puncture that is dilated to accept the tubing and leakage is almost never a problem. After cutting off excess tubing, the peritoneal collection tubing is then attached to the open faced conduit 30 forming the inlet port of the valve. The valve lies in an incision made through the subcutaneous fat 102. Some of the fat and deep fascia are dissected so that the valve housing 32 lies quite flat against the abdominal wall. This allows the skin 100 and subcutaneous tissue 102 to be easily closed over it without tension.

A tunnel is made with a vein and tubing passer designed for this purpose as is disclosed in U.S. Pat. No. 4,418,693 which is incorporated by reference into this application. The tip 28 of the venous tubing 22 is inserted into the internal jugular vein (or subclavian vein if that route is chosen)as is well known in the art. The venous tubing is inserted into the vein using the Seldinger technique.

The inside and outside surfaces of the plastic venous tubing 22 are treated to prevent clot formation on the outside of the indwelling venous tubing. One method involves bonding of a hydrophilic colloid to the surface of the venous tubing. For instance, polyvinylpyrolidone or heparin can be chemically bonded to the surface of the venous tubing by radiation. An alternative is the sulphonation of the plastic surface. These treatments render the plastic surface water wettable and less likely to induce platelet activation and clotting. The presence of a hydrophillic colloid on the surface of the tubing renders it thrombus resistant. The surface treatment may also be by sulphonation which in addition to rendering the surface wettable with water possesses unique anticoagulant properties. These treatments have an added advantage in that they prevent air bubbles from adhering to the surface of the tubing. Small bubbles are often difficult to dislodge. The venous tubing 22 also is provided with an opaque wall allowing identification by radiography.

Figure 20:
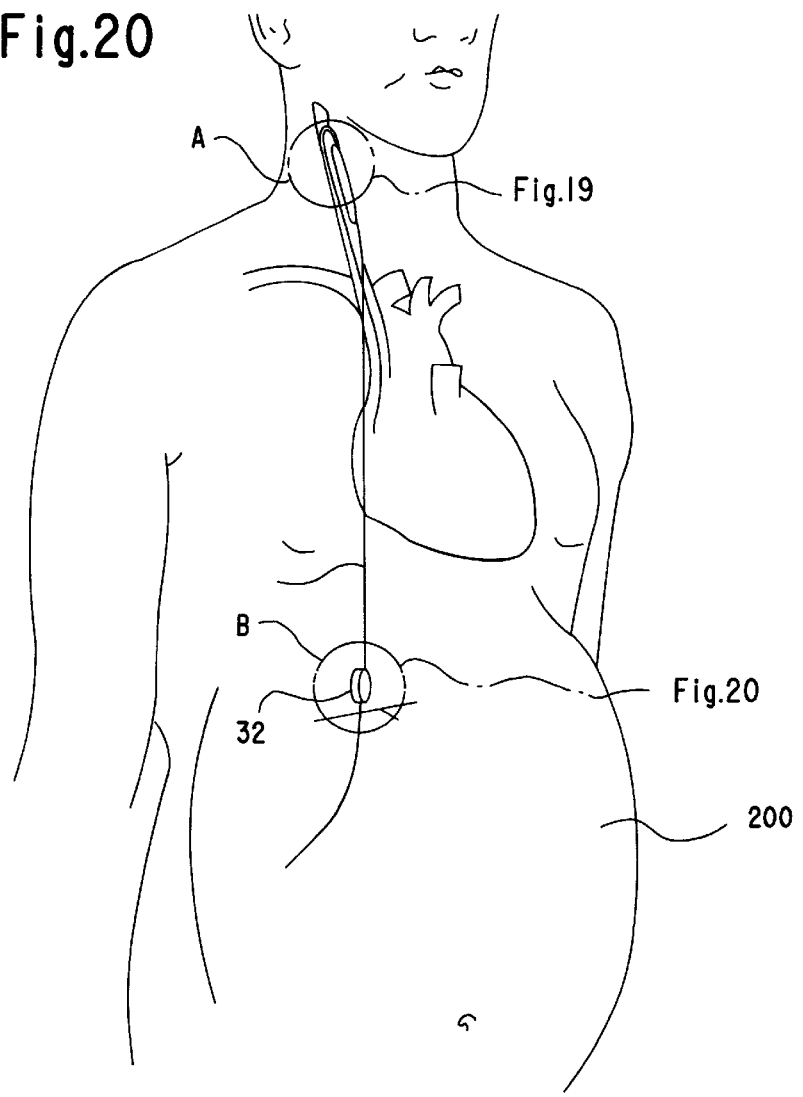
FIG. 20 is a schematic view of a patient after insertion of the inventive shunt assembly.
Figure 21:
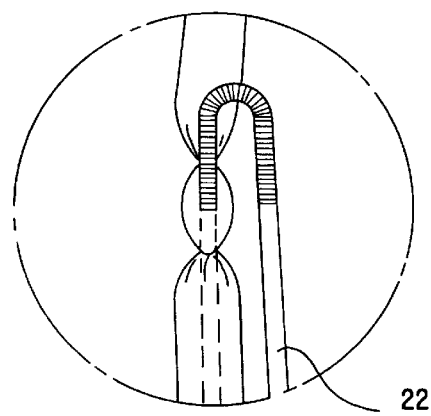
FIG. 21 is an exploded enlarged portion taken from circled area A in FIG. 20.
Figure 22:
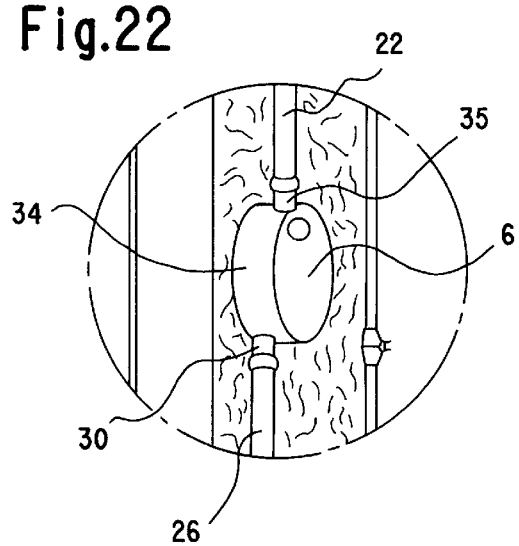
FIG. 22 is an exploded enlarged portion taken from circled area B in FIG. 20 showing the valve lying in the subcutaneous position after completion of the surgery.

The completed operation is illustrated in FIG. 20 with enlargements of various aspects shown in FIGS. 21 and 22. Formerly, a great deal of time was required to insert a peritoneovenous shunt. Ascitic patients are weakened and tolerate prolonged surgery poorly. Therefore, the design of the shunt including the valve, the venous and peritoneal collecting tubes and the apparatus supplied for its insertion all must be designed for a rapid insertion. The present shunt allows for percutaneous insertion of the tubes. The shunt and all of the tools required for rapid insertion are supplied to the surgeon as an integral unit in kit form.

FIG. 20 is a schematic view of a patient after insertion of the ascites valve. The venous tube extends from the atrio-caval junction down to the valve which is implanted subcutaneously parallel with the largest plane of the valve imbedded in the subcutaneous tissue parallel to the skin and muscle layers. The peritoneal tube extends from the lower end of the valve into the peritoneal cavity. The skin and subcutaneous tissue cover the valve without causing a protusion.

If the shunt does not occlude with occult peritonitis, the patient may present with a thrombus in the vena cava. This is not an uncommon happening. Such thrombosis is really a septic thrombophlebitis of the vena cava and attempts at lysis are usually unresponsive and may be associated with chills and fever. Nonetheless, it has been possible to place a new venous tube through an organizing thrombus once the infection has been aggressively treated. The thrombus is pierced with a pointed guide wire. An angioplasty balloon can then be threaded over the guide wire for balloon dilatation of the thrombus. The venous tube can then be advanced beyond the thrombus through the dilated passageway. In two such cases, long term patency has been restored. Late sepsis in cirrhotics is a serious but unrecognized problem for which the shunt offers no protection. Sepsis can occur after teeth extraction or even a respiratory infection. Shunted patients require continuous observation and repeated courses of prophylactic antibiotics during any febrile illness or a dental procedure.

If occult peritonitis is unrecognized and goes untreated, it is sometimes followed by an obliterative peritoneal fibrosis which mats multiple loops of bowel together and is called "cocoon formation". The inventors have seen only two such cases in 450 patients. In one case, the patient had a new shunt inserted for "fibrin flecks". The new shunt remained patent but the patient later developed intestinal obstruction. The patient expired 24 hours after he was seen and therapy initiated. At autopsy all of the intestines were matted into a small mass resembling a cocoon. No operative approach could have lysed all the matted bowel and it was impossible to demonstrate the exact site of obstruction even at autopsy. A similar fibrin sheath sometimes forms around peritoneal dialysis tubes.

The surgeon has an obligation to determine any cause of shunt failure and take remedial action. The present configuration of the shunt facilitates the investigation into shunt failure. Both injection ports on either side of the valve are utilized for diagnosis. First, the injection port on the peritoneal side of the valve is entered with a 22 gauge non-coring (Huber) needle and peritoneal fluid aspirated to look for fibrin flecks or turbidity. The fluid is cultured and sent for cell count and microscopy. At the conclusion of the aspiration 10 cc of Conray 60 or similar contrast agent is injected and an x-ray taken. The patient is then asked to make several forced inspirations against a resistance and the x-ray repeated. If the contrast agent has moved out of the shunt system the shunt is patent. If the shunt is patent, and the movement of ascetic fluid is sluggish shunt failure is probably due to a high central venous pressure of cardiac origin. The venous pressure can be measured through the venous injection port. If there is no movement of the contrast agent either the valve is clogged or the venous end is occluded by thrombus. To distinguish these two possibilities, the venous injection port is entered and 5 cc of contrast agent injected into the venous port. If there is no collection contrast agent at the tubing tip, there is no thrombus in the cava and the venous side of the shunt is clear. This means that the valve is non functional and must be replaced. The cause of occlusion is usually fibrin flecks even if the ascitic fluid appeared to be clear. All thrombi and occlusions should be treated as if arising from occult peritonitis and treated antibiotics.

In the foregoing description, the invention has been described with reference to a particular preferred embodiment, although it is to be understood that specific details shown are merely illustrative, and the invention may be carried out in other ways without departing from the true spirit and scope of the following claims.

What we claim is:

1. A shunt assembly for the transfer of body fluids which accumulate in a peritoneum cavity of a patient into a vascular system of the patient comprising a peritoneal tube connected to an inlet valve chamber of a plastic valve means with one end being positioned in the peritoneum, so that pressurized fluid transported from the peritoneum cavity will cause the valve means to open and pass the fluid under pressure into an outlet valve chamber and through a venous tubing which is connected thereto and into an access vein in a thorax of the patient, said valve means comprising a thin rigid transparent plastic housing defining two separated chambers, one chamber being provided with inlet port means comprising an opened faced conduit and the other chamber being provided with exit port means comprising an opened faced conduit, top and bottom covers removably secured to said housing allowing access to respective chambers when removed from said housing, a moveable valve seated in said housing adapted to move allowing fluid to flow from said inlet port housing chamber, past said valve and into said outlet port housing chamber said moveable valve member comprising a flexible conical shaped diaphragm means which rests against a valve seat formed in said housing between said outlet valve chamber and said inlet valve chamber, said valve diaphragm means moving away from said valve seat in response to a differential pressure exerted on it thereby permitting flow of the body fluid from the peritoneum through the valve housing and through the venous tube into an intrathoracic vein.

2. A shunt assembly according to claim 1 wherein said diaphragm means includes flexible strut means comprising a plurality of flexible struts secured at one end to a hollow conical member and a rim support member secured to a distal end of said struts.

3. A shunt assembly according to claim 2 wherein said rim support member is circular and defines a downwardly projecting flange from the circumference of said rim support member.

4. A shunt assembly according to claim 2 wherein said plurality of struts are at least four struts.

5. A shunt assembly according to claim 1 wherein said conical valve means defines a stepped interior chamber.

6. A shunt assembly according to claim 5 wherein said conical valve means stepped interior chamber defines an angled end.

7. An assembly according to claim 1 wherein said valve housing is constructed of polysulfone.

8. An assembly according to claim 1 wherein said valve means is constructed of silicon rubber.

9. An assembly according to claim 1 wherein said venous tubing has a tip surface bonded with heparin.

10. An assembly according to claim 1 wherein a hydrophilic colloid is bonded to the surface of the venous tubing.

11. A device for transfer of body fluids which accumulate in a peritoneum cavity into a vascular system comprising a peritoneal tube connected to an inlet of a transparent thin rigid plastic implantable valve housing holding a moveable valve means therein, said valve housing being implantable in the subcutaneous tissue of the patient, pressure differentials in fluids from the peritoneum cavity causing said valve means to open and pass the fluid under pressure therethrough into a venous tubing connected to an outlet of the valve means, a tip of said venous tubing being positioned in a major intrathoracic vein of a patient, said plastic housing including an inlet conduit with an open faced lumen and an outlet conduit with an open faced lumen with the axis of both conduits being substantially parallel to each other, said housing defining an inlet chamber communicating with said inlet conduit and an outlet chamber communicating with said outlet conduit, a valve means positioned between and separating said inlet and outlet chambers, said peritoneal tube being mounted to said inlet conduit and covering said open faced lumen and a venous tube mounted to said outlet conduit and covering said open faced lumen, said valve means including a valve member having a flexible diaphragm section which rests against a valve seat in said housing in a normally closed position and moves away from said valve seat in response to pressure exerted thereon to permit flow of the body fluid from the peritoneum through the valve housing and into the venous tube which empties into an intrathoracic vein.

12. A device for the transfer of body fluids as claimed in claim 11 wherein said valve seat has a truncated cone shape with a cylindrical wall positioned from the base of the truncated cone to form an angled space between said valve seat and said cylindrical wall.

13. An implantable valve for the treatment of ascites comprising a thin transparent disc shaped housing with integral valve seat means separating inlet and outlet reservoir chambers, each of said reservoir chambers communicating with respective axially aligned open faced conduit port means, top and bottom covers secured to said housing respectively closing said outlet and inlet chambers, said top cover being provided with marking indicia and defining a recess which fits on a nipple formed on said housing so that said top cover is always aligned to show fluid flow direction, a moveable valve seated in said housing seated on said valve seat means and held on said valve seat means in a normally closed condition, said valve being adapted to move in response to differential pressure of at least 1–4 cm of water allowing fluid to flow into and out of said housing chambers.

14. A one piece valve according to claim 13 wherein said moveable valve comprises a center support member, a plurality of elastomeric struts extending outwardly from said center support member, a circular rim member secured to the end of said elastomeric struts, said rim member being provided with a flange which extends transverse to a plane of the rim member and a frustrum conical diaphragm member mounted to said center support member, said diaphragm member defining a chamber with an inner wall defining said chamber being stepped to seat on a conforming valve seat means.

15. A valve according to claim 14 wherein said disc shaped housing is a transparent biocompatible plastic constructed of polysulphone.

16. A valve for implantation in the subcutaneous tissue of a patient suitable for the treatment of ascites and hydrocephalus comprising a thin transparent rigid plastic housing with an integrally molded conical valve seat and a cylindrical valve retaining wall encircling said conical valve seat and being spaced therefrom, said housing defining separated chambers, one of which is provided with an inlet port conduit formed with an open upper face and another chamber being provided with an exit port conduit formed with an open upper face, said inlet port conduit and said exit port conduit being positioned axially parallel to each other, top and bottom transparent covers secured to said housing enclosing said respective chambers, a moveable diaphragm valve seated in said housing on said valve seat, said moveable diaphragm valve being normally seated on a valve seat conforming to a shape of the diaphragm valve in a closed condition, said diaphragm valve being adapted to move away from said valve seat in response to a preset differential fluid pressure which can vary from 1 to 20 cm of water allowing fluid to flow through said inlet conduit port into said housing past said diaphragm valve and out said exit port conduit.

* * * * *